US00PP24482P2

(12) United States Plant Patent
Cho

(10) Patent No.: US PP24,482 P2
(45) Date of Patent: May 20, 2014

(54) ***COLOCASIA* PLANT NAMED 'MAUI GOLD'**

(50) Latin Name: *Colocasia esculenta*
Varietal Denomination: MAUI GOLD

(71) Applicant: University of Hawaii, Honolulu, HI (US)

(72) Inventor: John J. Cho, Paia, HI (US)

(73) Assignee: University of Hawaii, Honolulu, HI (US)

( * ) Notice: Subject to any disclaimer, the term of this patent is extended or adjusted under 35 U.S.C. 154(b) by 0 days.

(21) Appl. No.: 13/815,950

(22) Filed: Mar. 16, 2013

(51) Int. Cl.
*A01H 5/00* (2006.01)

(52) U.S. Cl.
USPC ..... Plt./373

(58) Field of Classification Search
USPC ..... Plt./373
See application file for complete search history.

(56) References Cited

U.S. PATENT DOCUMENTS

PP19,939 P2 * 4/2009 Cho ..... Plt./373

OTHER PUBLICATIONS

PlantHaven, Plant Variety Information Sheet.*

* cited by examiner

*Primary Examiner* — Anne Grunberg
*Assistant Examiner* — Keith Robinson
(74) *Attorney, Agent, or Firm* — James M. Weatherly; Cochran Freund & Young LLC

(57) ABSTRACT

A new cultivar of cultivar of *Colocasia* plant named 'MAUI GOLD' that is characterized by a combination of large sagittate-shaped chartreuse colored leaves with a glossy finish, bluish-purple colored piko, and petioles that are white to light yellow-green in color that turn light burgundy in color where they join the leaf 'Maui Gold' grows with a compact and clumping habit. In combination these characteristics distinguish 'MAUI GOLD' from all other varieties of *Colocasia* known to the inventor.

4 Drawing Sheets

This invention was made with Government support under Grant No. 2005-31100-06015/HAW00948H awarded by the U.S. Department of Agriculture. The Government has certain rights in this invention.

Genus: *Colocasia.*
Species: *esculenta.*
Denomination: 'MAUI GOLD'.

BACKGROUND OF THE INVENTION

The present invention relates to a new and distinct variety of *Colocasia* commonly known as the taro plant or elephant ears. *Colocasia* is grown as a food crop or for use as an ornamental for container or the landscape. The new cultivar is known botanically as *Colocasia esculenta* and will be referred to hereinafter by the cultivar name 'MAUI GOLD'.

*Colocasia* is a tuberous rooted perennial which is native to tropical Asia and Polynesia. It grows to 1.5-2 m in height from starchy tubers. The leaves of *Colocasia* are heart-shaped and very large in size. The tuberous roots are cooked and eaten as a starchy staple in many tropical areas. It is also grown as ornamental plants for the landscape in warmer climates or as a container plant in colder areas.

The new *Colocasia* variety named 'MAUI GOLD' is the product of a formal breeding program of the University of Hawaii, Kula. The purpose of the breeding program was to develop new commercial varieties by combining attributes not found in currently commercially available varieties.

'MAUI GOLD' is a seedling selection from the controlled pollination between the female parent breeding line '2001-52' (unpatented) and male parent breeding line '2002-41' (unpatented). Initially designated as '2004-05', 'MAUI GOLD' was derived from a single plant selected in 2004.

'MAUI GOLD' has large chartreuse colored glossy finish leaves with a bluish-purple colored piko. The lower petioles are white to light yellow-green in color and the upper section is light burgundy. The leaves are ⅓ to ½ times larger than its female and male parents. The male parent, '2002-41', exhibits greenish-purple colored leaves with a matte finish, a smooth margin, and light purple venation. The petioles are dark purple in color with a matte finish. The female parent, '2001-52' exhibits smaller violet leaves with a purple spot on the upper leaf surface at the point of leaf and petiole attachment and an undulating margin. The petioles are of a dark purple in color. In these aspects, this new variety differs from its parents.

The closest comparison variety known to the inventor is 'Elena' (unpatented), its closest commercial variety. 'MAUI GOLD' produces chartreuse colored glossy finish leaves as compared with 'Elena' that produces chartreuse colored matte finish leaves. 'MAUI GOLD' produces secondary lateral shoots that are closely attached to the mother plant as compared with 'Elena' that produces secondary lateral shoots on long stolons.

Asexual propagation of hulis of 'MAUI GOLD' began in 2004 in Kula, Hi. by the inventor using huli propagation whereby the apical shoots are separated from the plant by cutting the shoot at the top of the corm immediately above the newest leaf scar and planted. Evaluation in field and pot studies have shown the unique features of 'MAUI GOLD' to be stable, uniform, and reproduces true to type in successive generations of asexual propagation.

SUMMARY OF THE INVENTION

The following traits have been repeatedly observed and represent the distinguishing characteristics of the new *Colocasia* variety named 'MAUI GOLD'. In combination these traits set 'MAUI GOLD' apart from all other varieties of *Colocasia* known to the inventor. 'MAUI GOLD' has not been tested under all possible conditions and phenotypic differences may be observed with variations in environmental, climatic and cultural conditions, however, without any variance in genotype:

1. 'MAUI GOLD' exhibits large sagittate-shaped chartreuse colored glossy finish leaves with a bluish-purple colored piko.
2. The surface of the leaves of 'MAUI GOLD' is glossy.
3. 'MAUI GOLD' produces petioles that are white to light yellow-green in color turning light burgundy in color where they join the leaf.

BRIEF DESCRIPTION OF THE DRAWINGS

The accompanying color drawings

Figure 1:
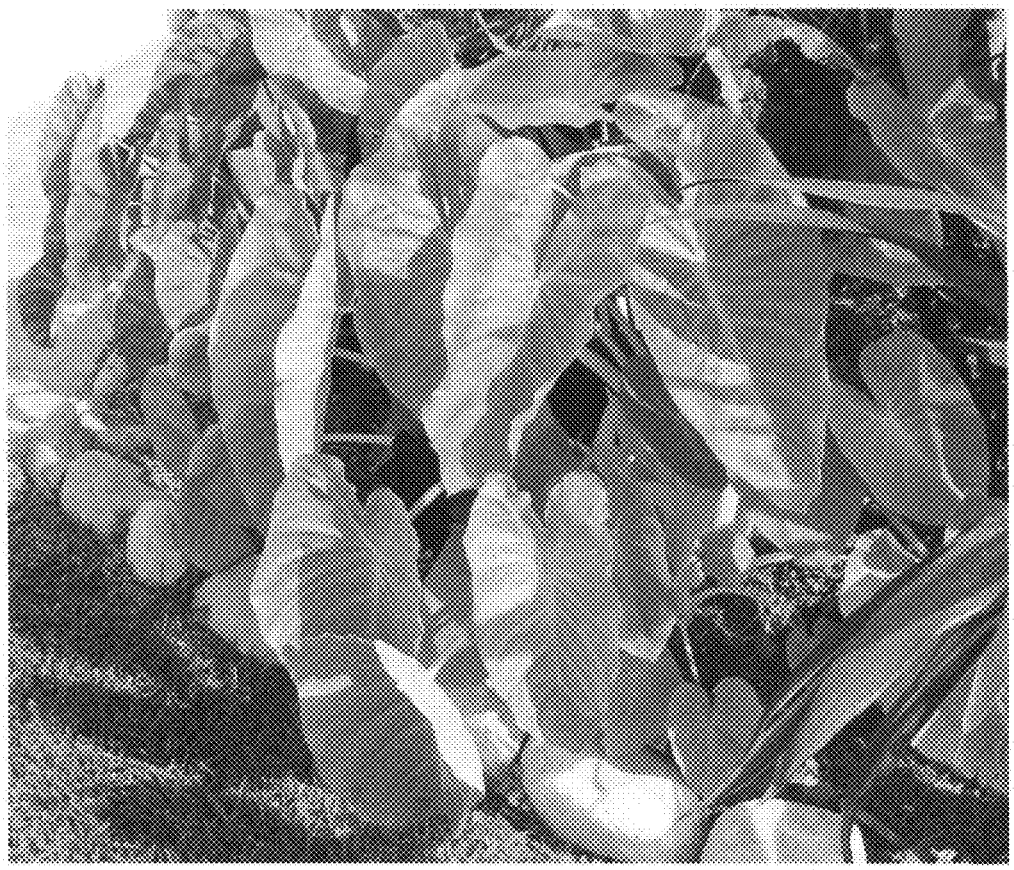
FIGS. 1 to 4 illustrate the overall appearance of 'MAUI GOLD' showing the colors as true as it is reasonably possible to obtain in colored reproductions of this type. Colors in the drawing may differ from the color values cited in the detailed botanical description, which accurately describe the actual colors of the new variety 'MAUI GOLD'.

The drawing labeled as FIG. 1 shows 'MAUI GOLD' grown from a huli after approximately 5 months.

Figure 2:
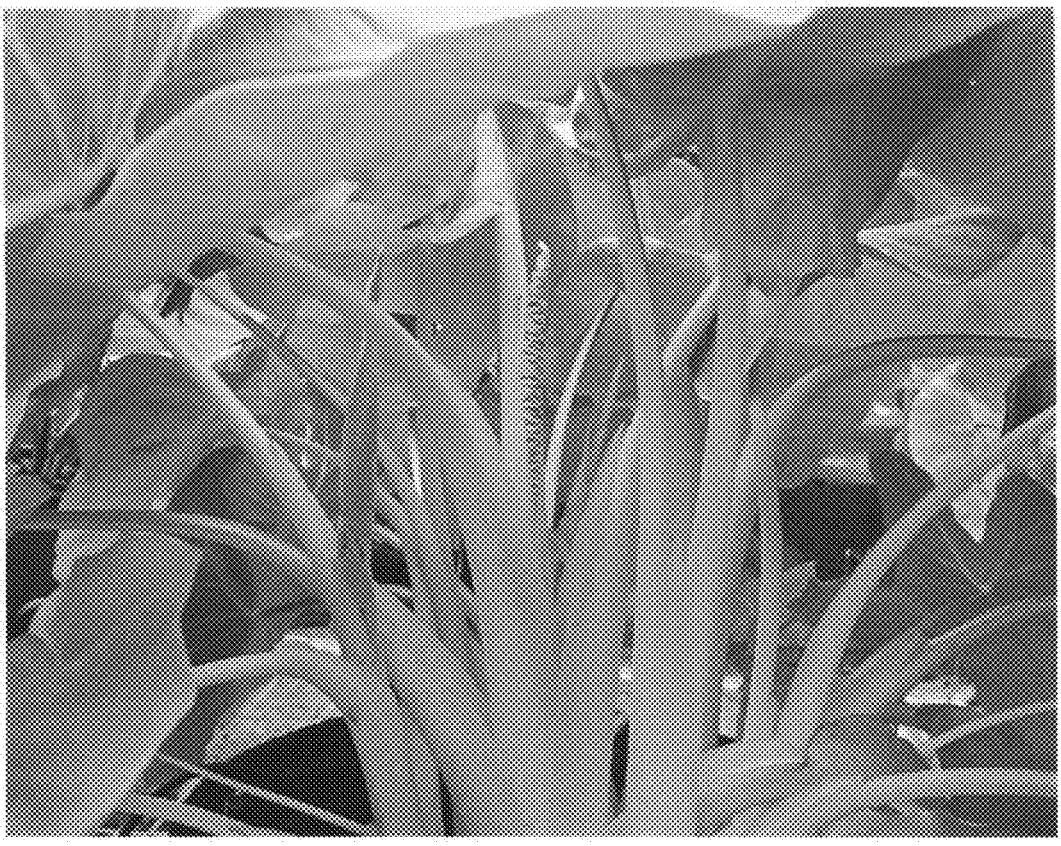

The drawing labeled as FIG. 2 shows the white to light yellow-green semi glossy colored petioles of 'MAUI GOLD' that turn light burgundy in color where they join the leaf.

Figure 3:
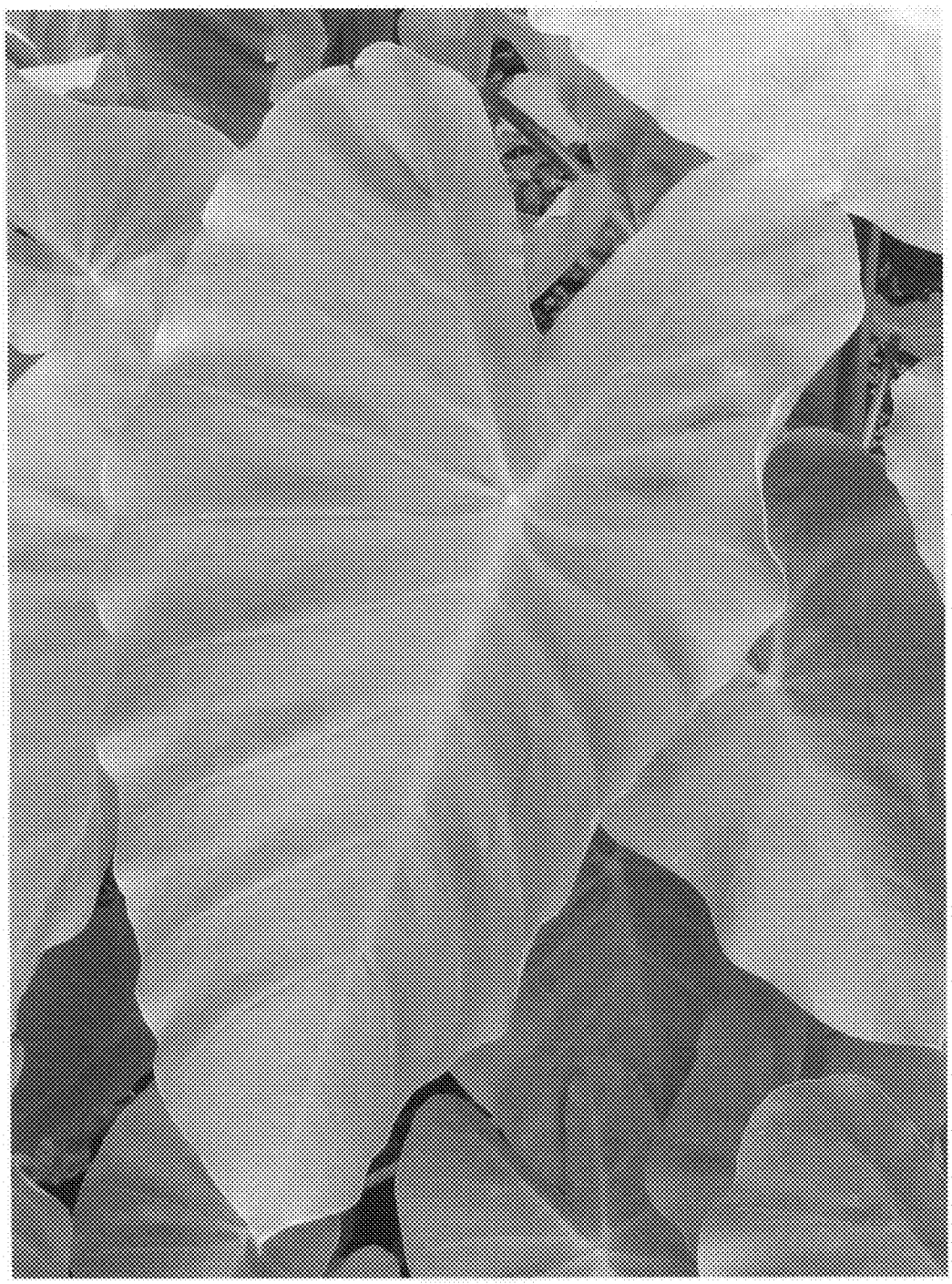

The drawing labeled FIG. 3 illustrates a large sagittate-shaped chartreuse colored leaf of 'Maui Gold' with a glossy finish and a bluish-purple colored piko.

Figure 4:
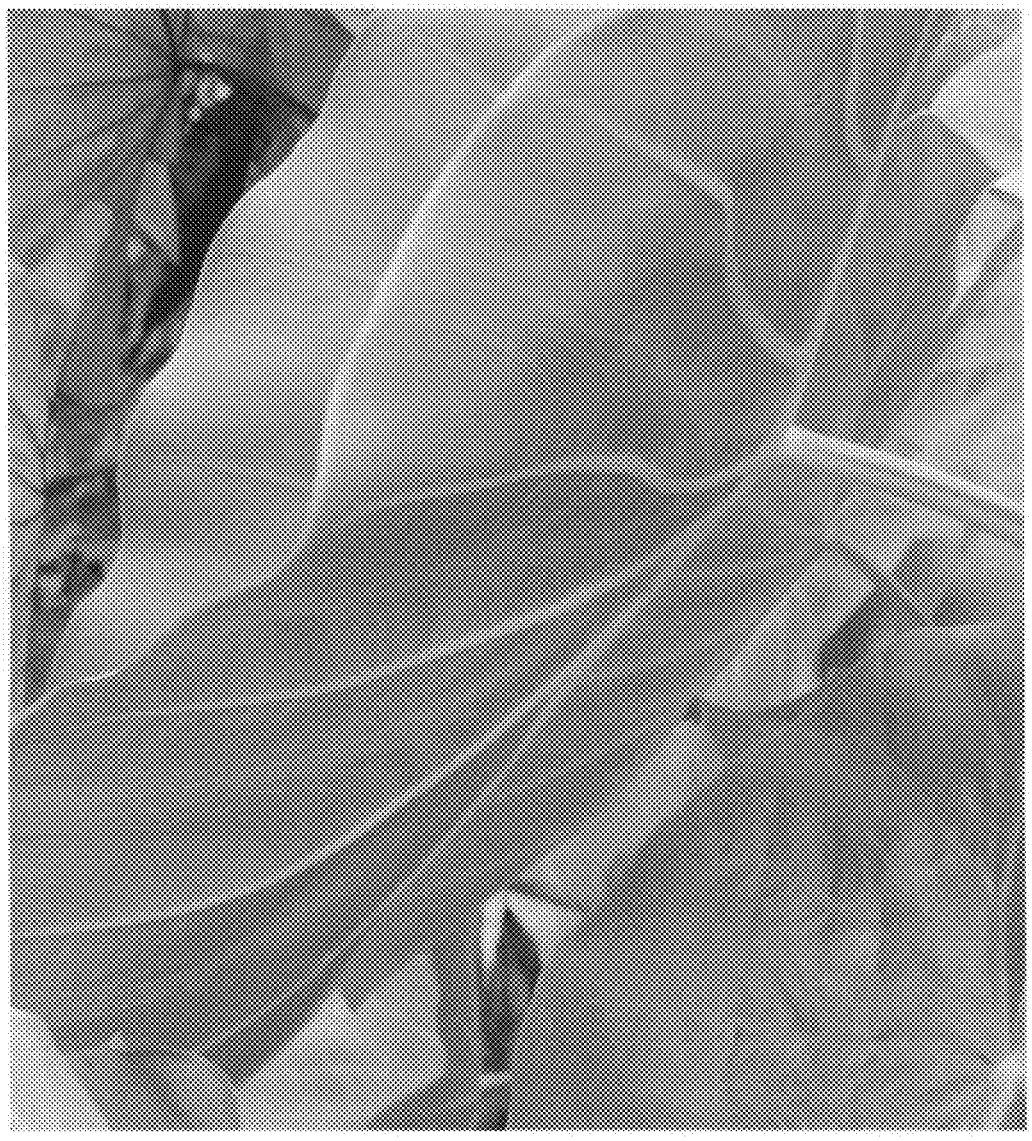

The drawing labeled as FIG. 4 shows the sheath or spathe that encloses the inflorescence or spadix of 'MAUI GOLD'.

All drawings have been made from plants which were approximately 5 months old from a division and which have been grown out-of-doors. No growth regulators have been applied.

BOTANICAL DESCRIPTION OF THE PLANT

The following is a detailed description of the new *Colocasia* plant named 'MAUI GOLD'. Data was collected from plants that were 3-6 months of age grown outside in Kula, Hi. as indicated. The color determinations are in accordance with the 2001 edition of The Royal Horticultural Society Colour Chart, London, England, except where general color terms of ordinary dictionary significance are used. The growing requirements are similar to other *Colocasia*.

Botanical classification:

Genus: *Colocasia.*

Species: *esculenta.*

Denomination: 'MAUI GOLD'.

Common name: Taro or elephant ears.

Plant use: Food, container or landscape plant.

Cultural requirements: Cultural requirements are well draining soil or growing media, full sun to partial shade.

Root system: Fibrous.

Plant vigor: Vigorous.

Plant growth habit: Upright, non-spreading.

Parentage:

*Female parent.*—'2001-52' (unpatented).

*Male parent.*—'2002-41' (unpatented).

Plant description: The plant has 4-6 suckers closely attached to the mother plant. A "mother plant" is the plant material which is first introduced into the soil to begin production. Typically, this plant material contains part of the huli and 2-3 leaf blades. This produces a "mother corm" which produces lateral shoots called 'cormels' which give rise to daughter plants. Daughter plants begin to appear above soil level about 2-3 months after planting of the mother plant.

Plant dimensions: Height — 65 cm to 68 cm; width — 85 cm to 88 cm.

Plant hardiness: USDA Zone 7b.

Propagation: Propagation is accomplished by huli propagation and by tissue culture.

Time to develop daughter plants: Appear above soil around 2-3 months after planting.

Crop time: 1.5 to 2.5 months.

Pest or disease susceptibility and resistance: No more or less susceptible to disease or pests than other cultivars.

Foliage:

*Number.*—On average, a 5 to 6 month old mother plant maintains 5 functional leaves at a time; each new leaf is produced approximately every 10 days until the corm matures.

*Petioles.*—Length: Up to 60 cm in length. Width: 0.5 cm×1.5 cm×2 cm (just below attachment to lamina x at the upper sinus x at the middle of the sinus). Color: 186A uppermost burgundy colored section, fading to 150D on lower yellow-green section. Sap color: Colorless.

*Leaf.*—Dimensions at maturity (5-6 months old): 32 cm in length and 21 cm in width. Average leaf sinus depth: 7.5 cm. Aspect: Erect with apex down. Shape: Sagittate lamina. Attitude: Oblique. Margins: Entire, slightly undulating. Apex: Pointed. Base: Peltate. Lamina appendages: Absent. Attachment: Petiolate with characteristic tissue formed at junction of leaf blade with the upper termination of the petiole. This area of the leaf tissue is also known as the "piko" and is evident by virtue of its upper surface color being the same color as the veins or darker. The principal veins radiate from the piko. Piko color: 186A. Leaf sheath: Open. Texture: Glossy. Leaf color (adaxial surface): 150A. Leaf color (abaxial surface): 149B. Venation: Palmate. Veins: Three principal veins radiating from the piko with the largest a midrib extending from the piko to the tip of the lamina with up to 12 pairs of secondary veins radiating from it. Vein color (adaxial surface): 150D. Vein color (abaxial surface): 150C.

Inflorescence, flowers and reproductive organs: The inflorescence arises from the leaf axils. The inflorescence is made up of a short peduncle, a spadix, and spathe. The spadix is botanically a spike, with a fleshy central axis to which the small sessile flowers are attached. The spadix is 9.5 cm to 10 cm long, with female flowers at the base, male flowers towards the tip, and sterile flowers in between, in the region compressed by the neck of the spathe. The extreme tip or appendage of the spadix has no flowers at all. The spathe is a large yellowish bract, 19.5 cm to 21.5 cm long, which sheathes the spadix. The lower part of the spathe is light-green (150B) in color and wraps tightly around the spadix and completely occludes the female flowers from view. The top portion of the spathe is yellow (13C) in color and is rolled inward at the apex, but is open on one side to reveal the male flowers on the spadix. The top and bottom portions of the spadix are separated by a narrow neck region, corresponding to the region of the sterile flowers on the spadix.

Seed: Seed is not produced naturally since male and female flowers within each inflorescence do not mature at the same time. Pollination can be achieved manually or in nature, only with the presence of small insect pollinators which are found in regions of genetic origin of the species, and not Hawaii.

The invention claimed is:

1. A new and distinct cultivar of *Colocasia* plant named 'Maui Gold' as described and illustrated herein.

* * * * *